United States Patent
Heyd et al.

(10) Patent No.: US 10,092,436 B2
(45) Date of Patent: Oct. 9, 2018

(54) ANKLE FOOT ORTHOSIS (AFO) AND METHOD OF MAKING THE SAME

(71) Applicant: Bracemasters International, LLC, New Berlin, WI (US)

(72) Inventors: Davin T. Heyd, Delavan, WI (US); William D. Falcon, Elkhorn, WI (US)

(73) Assignee: BRACEMASTERS INTERNATIONAL, LLC, New Berlin, WI (US)

( * ) Notice: Subject to any disclaimer, the term of this patent is extended or adjusted under 35 U.S.C. 154(b) by 245 days.

(21) Appl. No.: 13/837,636

(22) Filed: Mar. 15, 2013

(65) Prior Publication Data

US 2014/0276314 A1    Sep. 18, 2014

(51) Int. Cl.
A61F 5/01    (2006.01)

(52) U.S. Cl.
CPC .......... *A61F 5/0111* (2013.01); *A61F 5/0104* (2013.01)

(58) Field of Classification Search
CPC .... A61F 5/0102; A61F 5/0104; A61F 5/0111; A61F 5/0113; A61F 5/0116
USPC ............... 602/5, 23, 27, 28, 29, 65; 128/882
See application file for complete search history.

(56) References Cited

U.S. PATENT DOCUMENTS

| | | | |
|---|---|---|---|
| 1,037,441 A | 9/1912 | Collis | |
| 2,994,322 A | 8/1961 | Cullen et al. | |
| 3,333,353 A | 8/1967 | Garcia | |
| 3,970,083 A | 7/1976 | Carrigan | |
| 4,187,844 A | 2/1980 | Caprio, Jr. | |
| D255,384 S | 6/1980 | Finnieston | |
| 4,280,488 A * | 7/1981 | Polsky et al. | 602/27 |
| 4,489,719 A | 12/1984 | Lapenskie | |
| 4,863,779 A | 9/1989 | Daponte | |
| 4,878,505 A * | 11/1989 | Thanner | A61F 5/0111 128/882 |
| 4,998,537 A | 3/1991 | Rau | |
| D339,671 S | 9/1993 | Manning | |
| 5,370,604 A | 12/1994 | Bernardoni | |
| 5,456,976 A * | 10/1995 | LaMarca et al. | 442/221 |
| 5,472,414 A * | 12/1995 | Detty | 602/27 |
| 5,501,659 A | 3/1996 | Morris et al. | |
| 5,657,767 A | 8/1997 | Nelson et al. | |
| 5,713,837 A | 2/1998 | Grim et al. | |
| D394,112 S | 5/1998 | Duback et al. | |
| 5,814,002 A | 9/1998 | Nelson | |
| 5,853,380 A * | 12/1998 | Miller | A61F 5/0111 602/23 |
| 6,024,712 A | 2/2000 | Iglesias et al. | |
| 6,083,184 A | 7/2000 | Kenosh | |

(Continued)

FOREIGN PATENT DOCUMENTS

WO    WO 2011113473 A1 *    9/2011    ......... A61F 5/05841

OTHER PUBLICATIONS

The Richie Brace; Precision Orthotic Lab International; www.precisionorthotic.com/precision/products/richiebrace.htm; Copyright © 2004; 3 pages.

(Continued)

*Primary Examiner* — Keri J Nelson
(74) *Attorney, Agent, or Firm* — Husch Blackwell LLP

(57) ABSTRACT

A custom or pre-fabricated ankle foot orthosis provides tri-planar control of the ankle foot structure. The ankle foot orthosis includes a brace body made from a polyolefin elastomeric material, foam material and a closure mechanism.

30 Claims, 6 Drawing Sheets

(56) References Cited

U.S. PATENT DOCUMENTS

| | | | |
|---|---|---|---|
| 6,155,997 | A | 12/2000 | Castro |
| D440,661 | S | 4/2001 | Cionitti |
| 6,212,743 | B1* | 4/2001 | Cohen .......................... 24/713 |
| 6,394,971 | B1* | 5/2002 | Slautterback et al. .......... 602/27 |
| 6,517,505 | B1* | 2/2003 | Veldman ......................... 602/27 |
| 6,540,705 | B2 | 4/2003 | Norstrem et al. |
| 6,652,474 | B1 | 11/2003 | Quinn et al. |
| 6,663,584 | B2* | 12/2003 | Griesbach et al. ............. 602/75 |
| 6,767,332 | B1 | 7/2004 | Pardue et al. |
| D509,586 | S | 9/2005 | Lee |
| 7,014,621 | B2 | 3/2006 | Nelson |
| 7,018,351 | B1 | 3/2006 | Iglesias et al. |
| D548,846 | S | 8/2007 | Buethorn |
| D552,744 | S | 10/2007 | Verkade et al. |
| D559,988 | S | 1/2008 | Buethorn |
| 7,513,881 | B1* | 4/2009 | Grim .................... A61F 5/0585 128/882 |
| 7,651,472 | B2 | 1/2010 | Gaylord et al. |
| 7,691,076 | B2 | 4/2010 | Castro |
| 7,867,180 | B2* | 1/2011 | Cuypers ................. A61F 13/04 428/316.6 |
| 7,918,811 | B2 | 4/2011 | Lussier et al. |
| 7,950,676 | B2 | 5/2011 | Goldsmith et al. |
| D639,965 | S | 6/2011 | Wehsely-Swiczinsky |
| 7,993,295 | B2 | 8/2011 | Nelson |
| D649,650 | S | 11/2011 | Wehsely-Swiczinsky |
| D682,434 | S | 5/2013 | Heyd et al. |
| 8,512,269 | B1 | 8/2013 | Stano et al. |
| D696,409 | S | 12/2013 | Best et al. |
| D708,344 | S | 7/2014 | Best et al. |
| D722,382 | S | 2/2015 | Lee et al. |
| 2003/0083603 | A1 | 5/2003 | Nelson |
| 2004/0034316 | A1 | 2/2004 | Castro |
| 2005/0096576 | A1 | 5/2005 | Castro |
| 2009/0076428 | A1* | 3/2009 | Kay ...................... A61F 5/0111 602/27 |
| 2010/0094392 | A1* | 4/2010 | Nguyen et al. ............... 623/1.11 |
| 2011/0196276 | A1 | 8/2011 | Kuhn |
| 2014/0188026 | A1* | 7/2014 | Gaylord .......................... 602/27 |
| 2014/0213953 | A1 | 7/2014 | Heyd et al. |
| 2014/0243724 | A1* | 8/2014 | Dodin ............................ 602/27 |
| 2014/0276314 | A1 | 9/2014 | Heyd et al. |

OTHER PUBLICATIONS

Richie Brace—Custom Articulated Ankle Foot Orthosis; www.footcareexpress.com/services/richie_brace_php; Copyright © 2011; 5 pages.

PCT Notification of Transmittal of the International Search Report and the Written Opinion of the International Searching Authority, or the Declaration; PCT International Search Report; PCT Written Opinion of the International Searching Authority relating to International Application No. PCT/US11/58317, dated Feb. 13, 2012 (7 pgs.).

DRAFO DRG; Bracemasters International, LLC; www.bracemasters.com; Apr. 2010; 2 pages.

Need value? quality? results? Think DRAFO; Bracemasters International, LLC; www.bracemasters.com; Sep. 2010; 3 pages.

AS1 Ankle Brace—Active Ankle; www.activeankle.com; at least as early as Dec. 2012; 2 pages.

EZ Lacer Ankle Brace—Active Ankle; www.activeankle.com; at least as early as Dec. 2012; 2 pages.

CF PRO Ankle Brace—Active Innovations; www.activeankle.com; at least as early as Dec. 2012; 2 pages.

PRO MED Ankle Brace—Active Innovations; www.activeankle.com; at least as early as Dec. 2012; 2 pages.

Multi-Phase Ankle Brace—Active Innovations; www.activeankle.com; at least as early as Dec. 2012; 2 pages.

T1 Ankle Brace—Active Ankle; www.activeankle.com; at least as early as Dec. 2012; 2 pages.

T2 Ankle Brace—Active Ankle; www.activeankle.com; at least as early as Dec. 2012; 2 pages.

Volt Ankle Brace—Active Ankle; www.activeankle.com; at least as early as Dec. 2012; 2 pages.

Johnson, R. et al.; Comparative Study of Ankle Support Devices; Journal of the American Podiatric Medical Association; vol. 84, No. 3; Mar. 1994; available at www.activeankle.com; 1 page.

Parekh, S. et al.; Prophylactic Bracing Decreases Ankle Injuries in Collegiate Female Volleyball Players; University of North Carolina; University of Pennsylvania; at least as early as Dec. 2012; available at www.activeankle.com; 2 pages.

Gehlsen, G. et al.; Ankle Joint Strength, Total Work, and ROM: Comparison Between Prophylactic Devices; Athletic Training JNATA; vol. 26, Spring 1991; available at www.activeankle.com; 4 pages.

Gehlsen, G. et al.; Subtalar Joint Movement During Running on Camber: Comparison Between Prophylactic Devices; Ball State University; at least as early as Dec. 2012; available at www.activeankle.com; 1 page.

Siegler, S. et al.; Heel Pain Control Characteristics of the Active Ankle Brace; Drexel University; at least as early as Dec. 2012; available at www.activeankle.com; 1 page.

Siegler, S. et al.; The Three Dimensional Passive Support Characteristics of Ankle Braces; presented at the 1996 American College of Foot and Ankle Surgeons Meeting and Scientific Seminar; available at www.activeankle.com; 2 pages.

Power Lacer Ankle Brace—Active Ankle; www.activeankle.com; at least as early as Dec. 2012; 2 pages.

The DRAFO DRG—Dynamic Response Gauntlet—Practitioner's Guide; Bracemasters International, LLC; www.bracemasters.com; published after Oct. 28, 2011; 2 pages.

Ossur Form Fit® Ankle Brace; http://www.ossur.com/?PageID=13539; at least as early as Dec. 2012; 2 pages.

DRAFO Caregiver Guide; Bracemasters International, LLC; www.bracemasters.com; Apr. 2011; 2 pages.

DRAFO Selection Guide; Bracemasters International, LLC; www.bracemasters.com; Apr. 2011; 2 pages.

DRAFO Clinical Education Workshop; Bracemasters International, LLC; www.bracemasters.com; Apr. 2011; 2 pages.

DRAFO Introduction; Bracemasters International, LLC; www.bracemasters.com; Apr. 2011; 2 pages.

DRAFO Practitioner Toolbox; Bracemasters International, LLC; www.bracemasters.com; Apr. 2011; 2 pages.

DRAFO Sport—The Ultimate Solution for Athletic Ankle Bracing; Bracemasters International, LLC; www.bracemasters.com; May 2011; 2 pages.

DRAFO Sport advertisement; Bracemasters International, LLC; www.bracemasters.com; May 2011; 1 page.

The DRAFO Difference; Bracemasters International, LLC; www.bracemasters.com; Sep. 2011; 2 pages.

Excel Ankle Brace—Active Ankle; www.activeankle.com; at least as early as Dec. 2012; 2 pages.

* cited by examiner

ANKLE FOOT ORTHOSIS (AFO) AND METHOD OF MAKING THE SAME

FIELD

This disclosure relates to providing a custom or prefabricated ankle foot orthosis (AFO). The AFO provides tri-planar control of ankle foot structure inducing stability and control to the hind-foot, mid-foot, and forefoot. This disclosure protects against the results of Posterior Tibial Tendon Dysfunction (PTTD), Ankle Arthritis, and ankle weakness or instability of the ankle-foot structure.

BACKGROUND

Typical ankle foot orthoses use rigid plastic as the primary element of the device with a traditional design that provides less control and less comfort. This traditional design and approach often leads to gait compensation and more limited results for the patient.

The traditional leather ankle gauntlet has been a popular orthosis for nearly 25 years. Though widely accepted for a wide range of patient pathologies, its design features in many cases create problems. These traditional leather gauntlets are nearly impossible to adjust in the field, are difficult to clean, have limited durability, and require significantly more time to manufacture than simplified thermoplastic orthosis designs.

There exists a need in improving upon conventional AFO devices and traditional leather ankle gauntlets. There exists a need for an AFO device that is comfortable and provides needed support, and which can be conveniently fit for a user, including with regard to condition indications, such as ankle, subtalar or midtarsal instability, among others.

SUMMARY

The present disclosure provides an ankle foot orthosis comprising a combination of a closed cell polyethylene foam inner lining bonded to a polyolefin elastomeric material.

In an embodiment, an ankle foot orthosis, comprising: a brace body comprising closed cell foam inner lining bonded to a polyolefin elastomeric material outer layer, the brace body further comprising: a back portion; a medial side portion having a medial front edge; a lateral side portion having a lateral front edge; a sole portion in a plane at least partially horizontal to the medial and lateral side; a proximal edge; the medial front edge and the lateral front edge being configured for an overlapping arrangement; and a closure mechanism to tighten the ankle foot orthosis on a foot.

The present disclosure provide an ankle foot orthosis composed of a combination of specific materials varied in stiffness and texture to yield an ankle foot orthosis having an improved combination of support, flexibility and comfort that can be tailored to better meet the specific needs of each individual patient.

The ankle foot orthosis is structured to provide tri-planar control of the ankle foot structure inducing stability and control to the hind-foot, mid-foot, and forefoot. In an embodiment, the ankle foot orthosis comprises a brace body comprising a medial side portion, a lateral side portion, a medial front edge of the medial side portion, a lateral front edge of the lateral side portion, a sole portion in a plane at least partially horizontal to the medial and lateral side portions having an arch portion and a heel portion, and a back portion extending from the heel portion to an upper calf portion. In embodiments, the brace body comprises a minimum of two layers including a closed cell polyethylene foam inner layer and a polyolefin elastomeric material as an outer layer. Optionally, an additional material layer can be applied over the surface of the foam inner layer to enhance the texture and provide a soft interface with the foot, for example, a synthetic leather-like material or elastic fabric.

The present disclosure also provides a method of manufacturing an ankle foot orthosis. In an embodiment, the method comprises the steps of providing a mold of a lower extremity, forming a closed cell polyethylene foam material over the mold, forming an outer layer of a polyolefin elastomeric material over the prior layer on the mold to create a second bonded layer, setting closure mechanisms (e.g., lace loops) into the polyolefin elastomeric outer layer, and removing the mold from the material layers to produce the ankle foot orthosis. In at least some embodiments, mounting structures are formed or otherwise constructed in the desired shape and size to interface and enhance the closure connection connections.

The ankle foot orthosis of the disclosure is an improved alternative to traditional ankle foot orthoses (AFOs), providing a broad range of features and benefits that address the limitations of traditional AFOs and leather ankle gauntlets. The present thermoplastic ankle foot orthosis is hygienic, waterproof, easily cleaned, and is readily adjustable at fitting utilizing a modest heat application. The present device provides more comfort with flexible control, and is more durable than traditional ankle foot orthoses. The device has a slim, low profile design that fits inside most shoes. The orthosis of the disclosure provides alternatives to achieving the required level of rigidity and performance that best addresses the needs of each patient's condition covering a broad range of neurological and orthopedic pathologies. The improved AFO provides a soft interface with the patient's foot to enhance comfort and alternatives for closure mechanisms.

BRIEF DESCRIPTION OF THE DRAWINGS

Preferred embodiments of the disclosure are described below with reference to the following accompanying drawings, which are for illustrative purposes only. Throughout the following views, the reference numerals will be used in the drawings, and the same reference numerals will be used throughout the several views and in the description to indicate the same or like parts.

DETAILED DESCRIPTION

Embodiments of the disclosure relate to an ankle foot orthosis (AFO) and methods of making the orthosis. The AFO can be custom-made or pre-fabricated, and provides tri-planar control of the ankle foot structure inducing stability and control to the hind-foot, mid-foot, and forefoot sections. The AFO of the disclosure helps protect against ankle weakness and/or instability of the ankle-foot structure.

Figure 3:
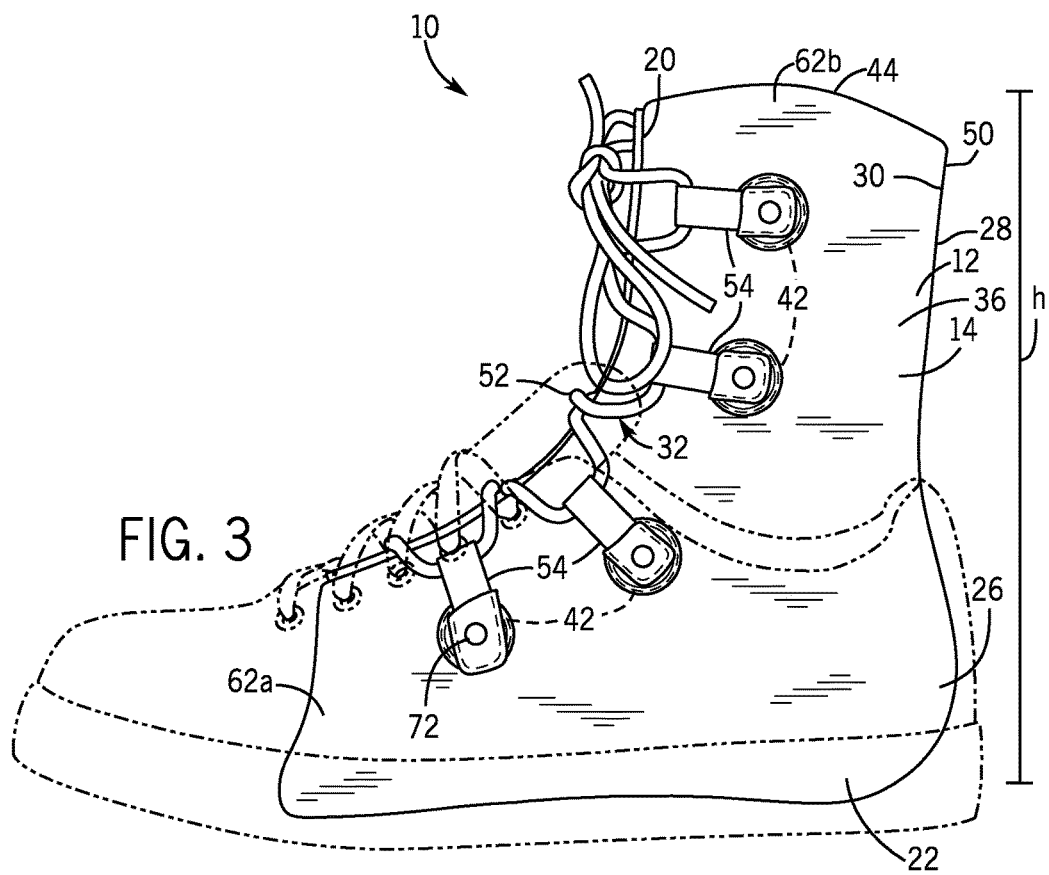
FIG. 3 is a medial side view of the ankle foot orthosis of FIG. 1 positioned inside a shoe (shown in phantom).

An embodiment of an ankle foot orthosis 10 according to the disclosure is described with reference to FIGS. 1, 3 and 4. The orthosis can be used in combination with a standard shoe (shown in phantom in FIG. 3). The orthosis is designed to be worn over a sock and inside the shoe without the need to increase the shoe size to accommodate the orthosis. The orthosis is in the general shape of a toe-less boot.

Figure 1:
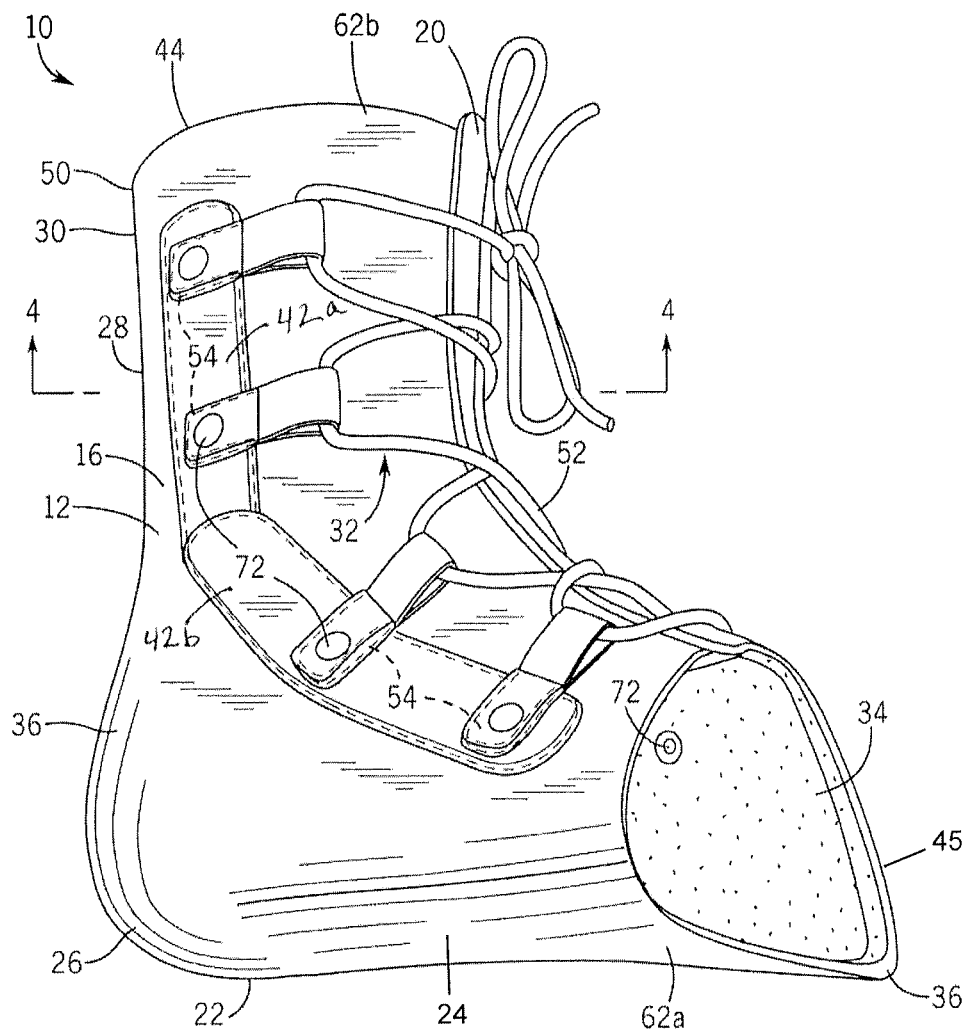
FIG. 1 is a perspective view of an embodiment of an ankle foot orthosis according to the disclosure.
Figure 4:
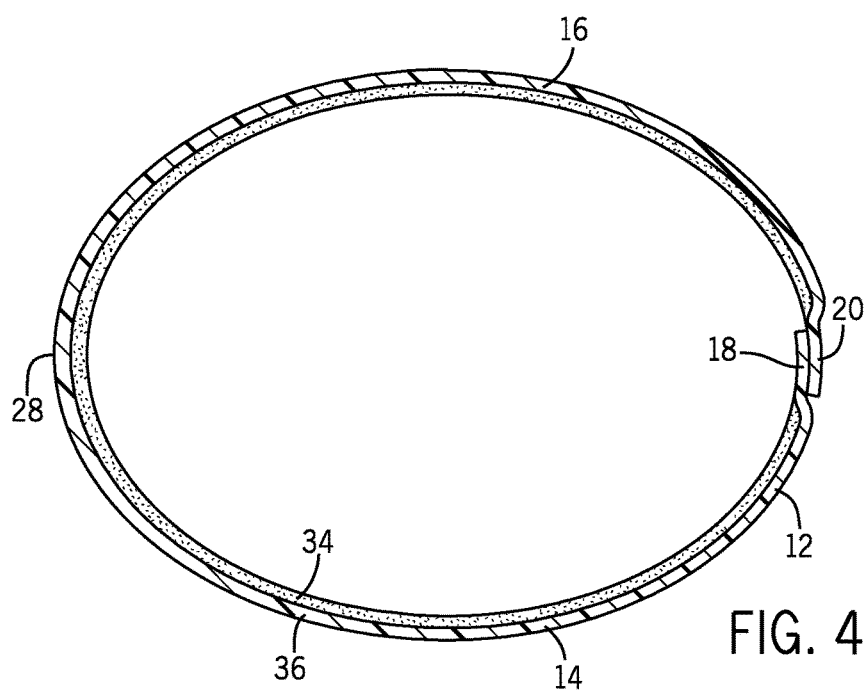
FIG. 4 is a cross-sectional view of the ankle foot orthosis of FIG. 1, taken along line 4-4 of FIG. 1.

Referring to FIGS. 1 and 4, the ankle foot orthosis 10 comprises a brace body 12 having a medial side portion 14, a lateral side portion 16, a medial front edge 18 of the medial side portion 14, a lateral front edge 20 of the lateral side portion 16, a sole portion 22 having an arch portion 24 (at about mid-foot) and a heel portion 26, and a back portion 28 extending from the heel portion 26 to an upper calf portion 30. The sole portion 22 is in a plane at least partially horizontal to the medial and lateral side portions 14, 16 of the brace body 12. As can be seen, at least a portion of the sole portion 22 is at least partially perpendicular to the medial and lateral side portions 14, 16 of the brace body 12. The ankle foot orthosis 10 further includes a closure mechanism 32 to tighten and secure the orthosis to the foot. The brace body 12 has a proximal edge 44 and a distal edge 45. FIGS. 1 and 3 are lateral and medial side views, respectively, of the ankle foot orthosis 10.

As illustrated, the brace body 12 comprises a laminated structure of at least two material layers including an inner layer 34 and a polyolefin elastomeric outer layer 36. The inner layer 34 is composed of a closed cell polyethylene (PE) foam, which, in embodiments, is at least 1.5 mm thick, preferably at least 3.0 mm thick, up to 4.5 mm thick. Closed cell PE foams are commercially available, for example, under the tradenames Volara® from Sekisui Voltek, LLC (Lawrence, Mass.), and Aliplast from AliMed, Inc. (Dedham, Mass.). Sheets of closed cell polyethylene foam are commercially available.

The outer layer 36 is composed of a rigid or semi-rigid thermoplastic material, preferably a polyolefin elastomeric material having thermoforming capabilities. In embodiments, the outer layer 36 is at least 2.0 mm thick, preferably at least 3.0 mm thick, up to 5.0 mm thick. In an embodiment, the polyolefin elastomeric material is an ethylene-butene copolymer or an ethylene-octene copolymer having a melt index range at 190° C. of less than 0.5 to 30 g/10 min (measured according to ASTM D 1238), a density of 0.857 to 0.910 g/cm$^3$ (measured according to ASTM D 792), a melting range of 36° C. to 104° C., a Shore A Hardness of 56 to 96 (ASTM D 2240), and a flexural modulus from 3 to 110 MPa (measured according to ASTM D 790). In another embodiment, the polyolefin elastomeric material is an ethylene-butene copolymer having a density of 0.885 g/cm$^3$ (measured according to ASTM D 792), a melt index of 2 g/10 min (2.16 kg @ 190° C. measured by ASTM D 1238), a Mooney Viscosity of 13 (ML 1+4@121° C., measured according to ASTM 1646), a Shore A durometer hardness of 82 (measured according to ASTM 2240) and an ultimate tensile strength of 11.2 MPa (508 mm/min measured according to ASTM D 638). Polyolefin elastomers are well known and commercially available, for example, ENGAGE® ethylene/α-olefin copolymers available from The Dow Chemical Company.

The closure mechanism 32 may include laces with a series of holes, eyelets, loops or hooks, Velcro® strips (available from Velcro USA, Inc.), elastic closures, cinched straps, zippers, snaps, buttons, hooks, clasps or other suitable fastener. In embodiments, when the closure mechanism 32 is engaged, the medial front edge 18 and the lateral front edge 20 of the brace body overlap, as shown in FIG. 4, such that the brace body does not require a separate tongue element. The overlap can be from 0.125 inches to 1.5 inches (0.32 cm to 3.8 cm), for example, 0.25 inch to 1.0 inch (0.64 cm to 2.5 cm).

As illustrated in FIG. 1, in an embodiment, the closure mechanism 32 is in the form of a lace 52 that cooperates with two or more lace loops 54 positioned at the distal section 62a of the brace body 12 (or the region that would typically reside inside the shoe) to engage the lace 52 and tighten and secure the ankle foot orthosis 10 onto the subject's foot.

Figure 2:
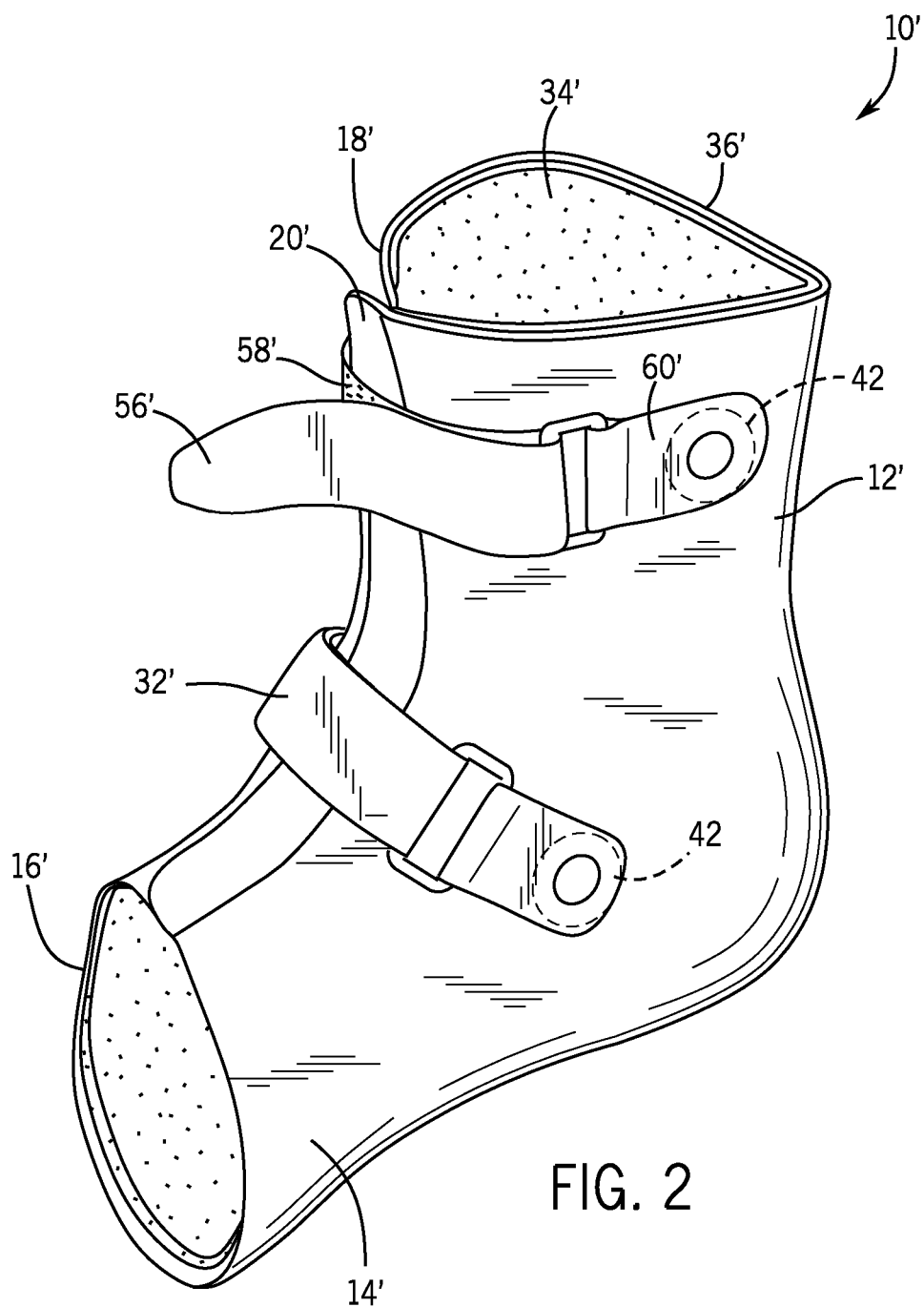
FIG. 2 is a perspective view of another embodiment of an ankle foot orthosis according to the disclosure.

In another embodiment shown in FIG. 2, the closure mechanism 32' is a hook and loop fastening mechanism in the form of an attachment strap 56' as a first Velcro part with a one end secured on the lateral side portion 16' of the brace body 12', and a loop element 60' secured on the medial side portion 14'. The second end of the attachment strap 56' is inserted through the loop of the loop element 60', pulled back and attached to a cooperating second Velcro part 58' to tighten the ankle foot orthosis 10' onto the person's foot and ankle.

Referring again to FIG. 1, the brace body 10 includes one or more mounting structures 42 which provide an enhanced attachment point or region for the respective lace loops 54, and particularly, the respective bases of the lace loops. In accordance with at least some embodiments, one or more of the mounting structures 42 comprises a non-metallic circularly-shaped (or disc-shaped) structure, although other shapes are contemplated and considered in the scope of the present disclosure. In at least some embodiments, the mounting structures can include material made in whole or in part from nylon. While not shown, such mounting structure 42 can also be used in conjunction with, as so as to provide enhanced securing of one or more of the plurality of loop elements 60' shown in FIG. 2.

Figure 8:
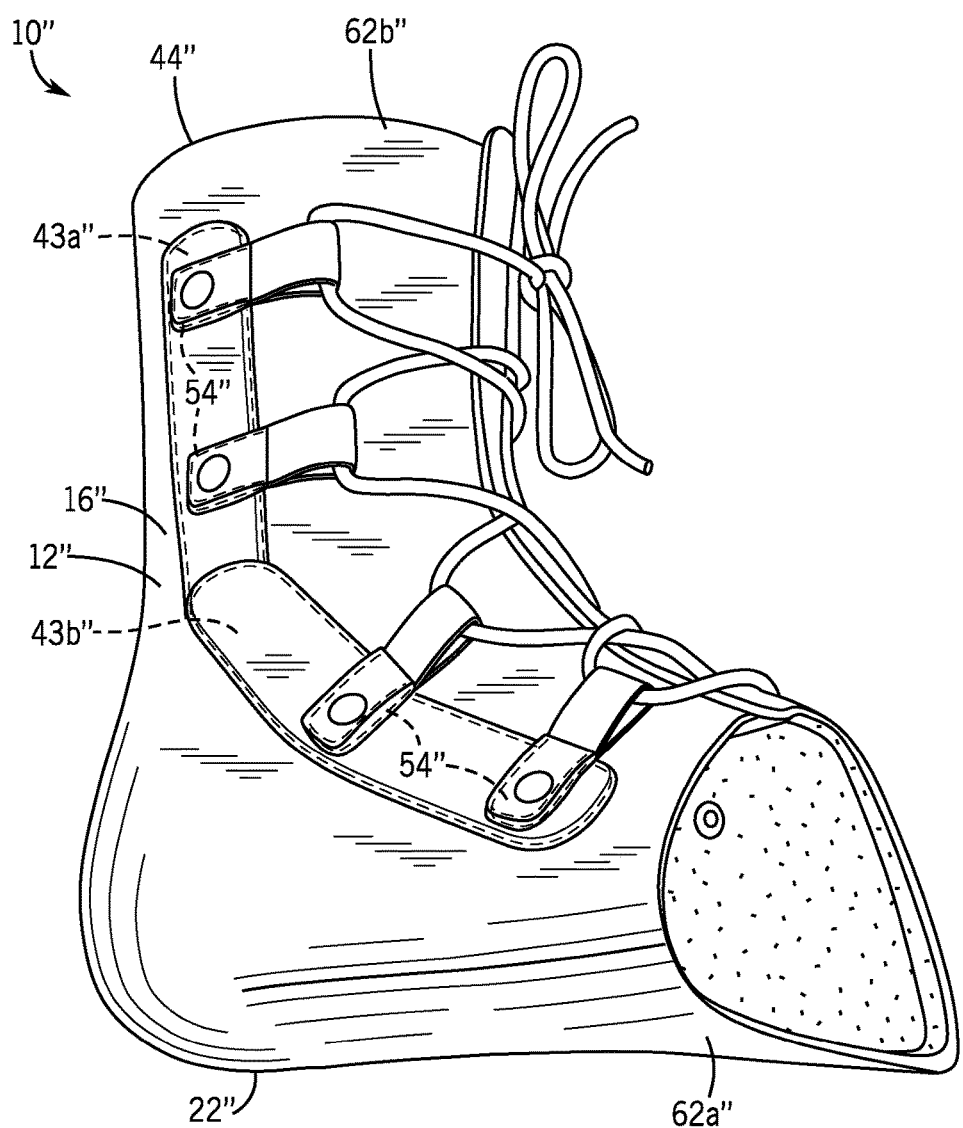
FIG. 8 is a perspective view of another embodiment of an ankle foot orthosis according to the disclosure.

As shown in FIG. 8, in accordance with alternative embodiments, an orthosis 10" is provided having a brace body 12" and can optionally include additional structures that take the form of one or more strips 43a" and 43b" that can extend, so as to secure, a multiplicity of lace loops 54". In some embodiments, such strips 43a" and 43b" extend from the distal section 62a" near the proximal edge 44" of the brace body 12" on the lateral side portion 16", to or toward the sole portion 22" and is in overlapping contact with the second portion 43b" which extends further in the distal section 62a" of the brace body 12". Additional strips can be similarly included on the medial side portion (not shown) of the brace body 12". Strips 43a" and 43b" can take any of variety of shapes and sizes, but it is contemplated that they are of sufficient size and shape to permit sufficient securement of the multiplicity of lace loops 54" while remaining durable and generally light weight. In at least some embodiments, the additional structures are configured to enhance the rigidity of at least a portion of the brace body and/or the lace loop closure mechanisms.

In some embodiments, the brace body further includes an interface layer (not shown) that is applied over the foam inner layer (to enhance and provide a soft interface with the subject's foot. The interface layer can be, for example, a synthetic leather-like material (e.g., Clarino® artificial leather), a synthetic elastic fabric (e.g., Lycra® material), or other soft material.

Optionally, a layer of a synthetic leather-like material (e.g., Clarino® artificial leather) or a synthetic elastic fabric (e.g., Lycra® material) can be applied over the surface of the foam inner layer, or a pre-laminated polyethylene foam with a bonded synthetic layer, to provide an interior interface with the foot to enhance the texture of the soft interface.

Method of Manufacture

Figure 7:
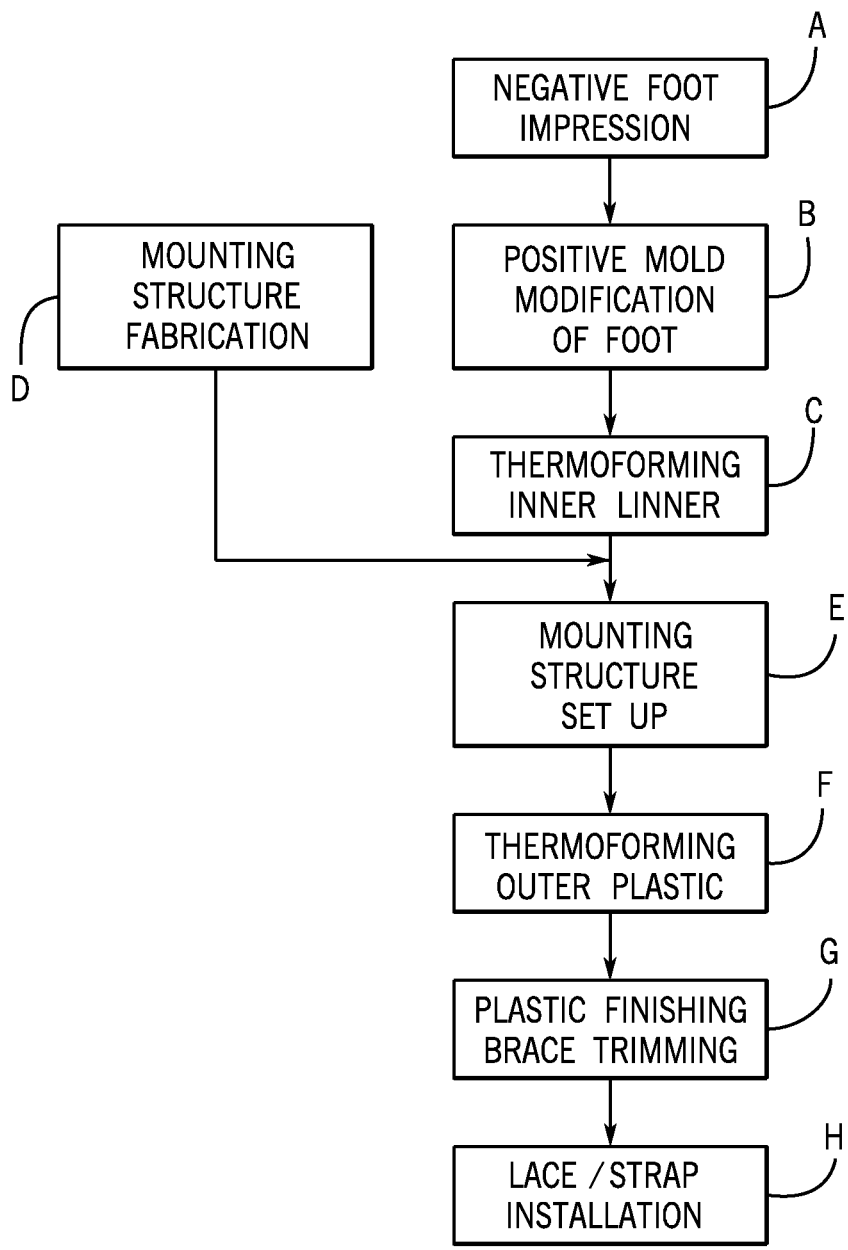
FIG. 7 is a block diagram of an embodiment of a process for making an ankle foot orthosis according to the disclosure.

FIG. 7 provides a process flow diagram of a method of manufacture of an ankle foot orthosis according to the disclosure.

Figure 5:
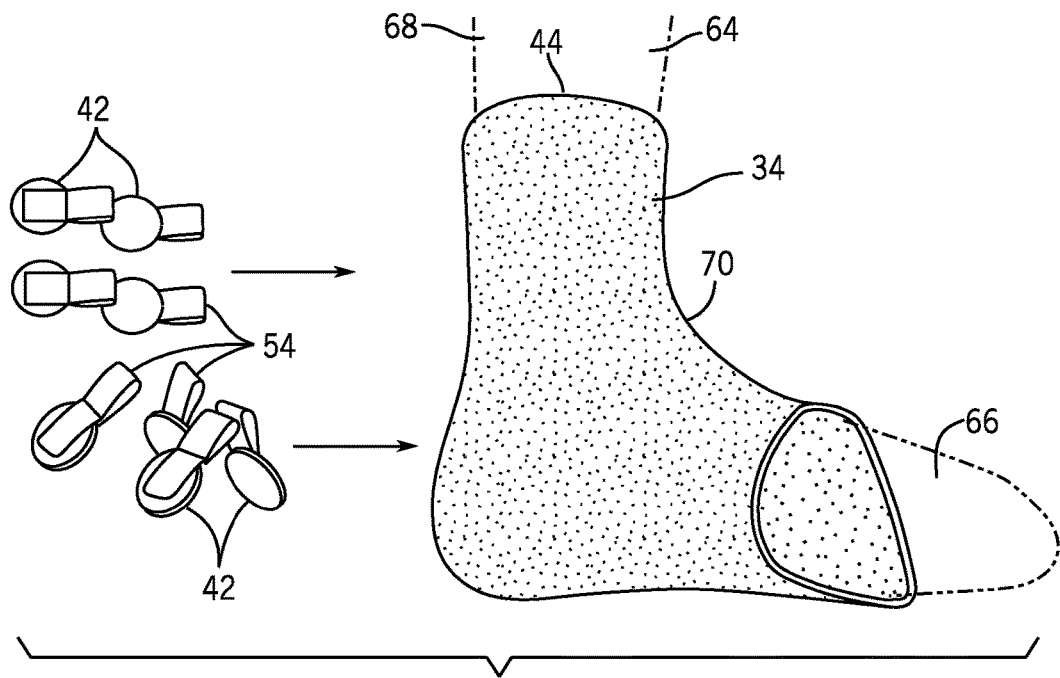
FIG. 5 is perspective view of the ankle foot orthosis of FIG. 1, showing the inner layer situated on a mold (shown in phantom).
Figure 6:
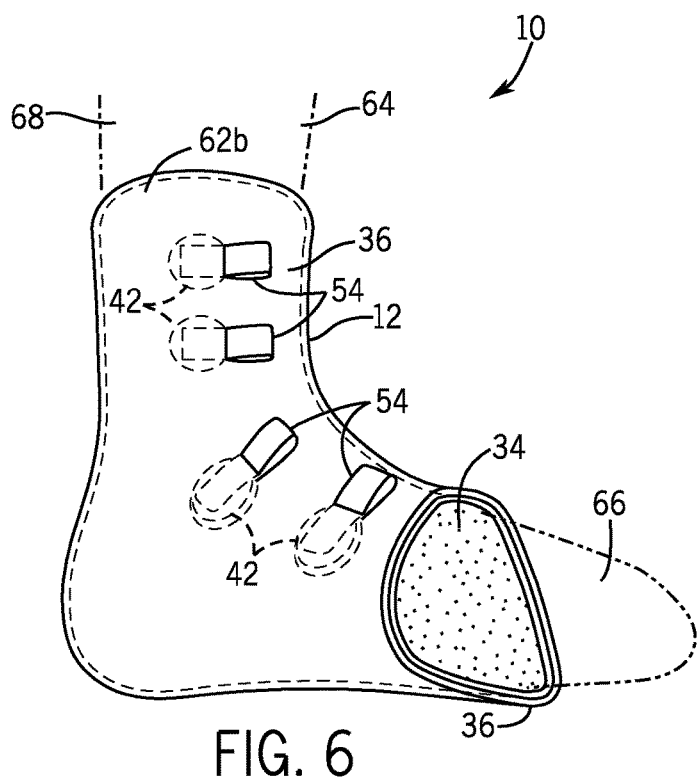
FIG. 6 is a perspective view of the ankle foot orthosis of FIG. 5, in a subsequent process step showing the inner layer and the applied outer layer.

In first steps A and B, a mold 64 (e.g., plaster, wax, metal, wood, epoxy molds) of a patient's lower extremity is provided, as shown in phantom in FIG. 5. The mold 64 may be created from a 3D image or negative cast of the patient's extremity. Alternatively, instead of a mold being made from a patient's scan or cast, the mold may correspond to a pre-fabricated size. Thus, a patient may choose a pre-fabricated standard size that most closely fits their foot size. The correct size is determined by measuring the instep of a patient by placing a flexible tape around the instep and heel with the ankle at 90 degrees. The measurement and patient's shoe size are used to determine the best pre-fabricated size on a sizing chart.

In a typical fabrication approach, the mold 64 to be used for the device being fabricated is mounted in a horizontal, tubular vacuum fixture. In a step C, a closed cell polyethylene foam lining material (for inner layer 34) is heated in sheet form and draped over the mold, from the posterior around to the anterior, thus establishing a straight seam from the toe through the instep and up past the proximal edge of the mold, thus enabling a seal around the tubular vacuum fixture. Vacuum is applied, creating an intimate capture by the closed cell polyethylene lining material 34 of the mold 64, as shown in FIG. 5. In at least some embodiments, mounting structures 42, described above, are provided. In an alternative embodiment, additional structures, such as strips 43a" and 43b" (FIG. 8), may be also be provided.

An alternate method incorporates a slightly altered mold geometry, designed to accommodate mounting on a vacuum table, where the closed cell polyethylene foam lining material is mounted in a frame, heated, and brought down over the mounted mold. The closed cell polyethylene foam lining material seals against the table which is connected to a similar vacuum source, thus creating a similar seam and intimate capture of the mounted mold by the closed cell polyethylene lining material.

After the foam liner (inner layer 34) has cooled sufficiently, strategic areas of the closed cell polyethylene liner are cut away from the mold 64 to expose the distal toe 66, the proximal surface 68 of the mold 64, and an anterior strip 70 approximately 1.25-inches (3.2 cm) wide extending from the toe 66 to approximately ½-inch (1.3 cm) from the proximal edge 44. These cut outs provide for sufficient vacuum for subsequent thermoforming steps as well as reducing bulk in the instep region where the finished device will overlap.

In a step D, mounting structures 42 are constructed by cutting or otherwise providing a portion of nylon material in the desired shape.

In a step E, the bases of the lace loops 54 are placed over mounting structures 42 (described previously) on the distal section 62a (or the region that would typically reside inside the shoe). Alternatively, Velcro fasteners can be placed on the exterior of the brace body 12 on the distal section 62a. In an embodiment, the bases of the lace loops 54 are heat welded or ultrasonic welded together.

In a next step F, the polyolefin elastomeric material to form the outer layer 36 is thermoformed over the assembly, typically using a method nearly identical to the process used for the closed cell polyethylene lining material 34. During thermoforming, the polyolefin elastomeric material outer layer 36 is heated to a temperature from 225° F. to 250° F. and placed over the mold 64 and the lace loops 54, that are placed over the mounting structures 42, to produce the brace body 12. In an embodiment, after the polyolefin elastomeric material for the outer layer 36 is draped over the mold 64 from the posterior around to the anterior thus establishing a straight seam from the region of the toe 66, through the instep (sole portion 22) and up past the proximal edge 68 of the mold 64, a vacuum is used to seal the polyolefin elastomeric material outer layer 36 over the mold and the lace loops 54. The vacuum can be maintained until the polyolefin elastomeric material outer layer 36 returns to room temperature. The mold 64 is then removed once the polyolefin elastomeric material outer layer 36 has cooled to room temperature to produce the ankle foot orthotic 10.

In a next step G, finishing and trimming of the plastic layers of the brace body is performed.

In a next step H, a cut is made in the polyolefin elastomeric material outer layer 36 across the width of the distal base of a lace loop 54 from which the lace loop 54 is pulled through to partially expose the lace loop 54 for future lacing. Fasteners 72 are added to further secure the base of the lace loops 54, outer layer 36, and the foam inner layer 34 together. Laces can be added through the lace loops 54.

In an embodiment, the height of the anterior and dorsal surfaces of the mold are such that the medial front edge 18 and the lateral front edge 20 may be overlapped when the ankle foot orthosis is tightened by the closing mechanism 32, as illustrated in FIGS. 1 and 2.

Additionally, in an embodiment, the closed cell polyethylene lining material (inner layer 34), and the base of the lace loops 54 are laminated in the brace body 12 such that a layer of a synthetic fabric (e.g., Clarino or Lycra) is first placed on the mold, or use a pre-laminated foam with a bonded synthetic layer, followed by the placement of the polyethylene foam inner lining material (34), and the base of the lace loops 54. Then the outer layer 36 of polyolefin elastomeric material is placed over the lace loops 54 thereby encapsulating the lace loops in the brace body. Other closure mechanisms besides lace loops and laces are contemplated and considered within the scope of the disclosure.

It is specifically intended that the present disclosure not be limited to the embodiments and illustrations contained herein, but include modified forms of those embodiments including portions of the embodiments and combinations of elements of different embodiments as come within the scope of the following claim.

We claim:
1. An ankle foot orthosis, comprising:
   a brace body comprising closed cell foam inner lining bonded to an outer layer consisting essentially of a polyolefin elastomeric material selected from the group consisting of an ethylene/butene copolymer and an ethylene/octene copolymer, wherein the outer layer substantially covers the inner lining, the brace body further comprising:
a back portion;
a medial side portion having a medial front edge;
a lateral side portion having a lateral front edge;
a sole portion; and
a proximal edge;
the medial front edge and the lateral front edge being configured for an overlapping arrangement; and
a closure mechanism to tighten the ankle foot orthosis on a foot,
wherein the ethylene/butene copolymer or ethylene/octene copolymer of the outer layer has a melt index at 190° C. of less than 0.5 to 30 g/10 min, a density of 0.857 to 0.910 g/cc, a melting range of 36° C. to 104° C., a Shore A Hardness of 56 to 96, and a flexural modulus from 3 to 110 MPa.

2. The ankle foot orthosis of claim 1, further comprising a material layer bonded to the foam inner lining.

3. The ankle foot orthosis of claim 2, wherein the material layer is selected from the group consisting of a synthetic leather material and a synthetic elastic fabric.

4. The ankle foot orthosis of claim 1, wherein the closure mechanism comprises laces, loops, hook and loop fastener, elastic, fasteners, or a combination thereof.

5. The ankle foot orthosis of claim 1, wherein the closure mechanism comprises laces and lace loops.

6. The ankle foot orthosis of claim 1, being structured for insertion into a shoe.

7. The ankle foot orthosis of claim 1, wherein at least a portion of the sole portion is at least partially perpendicular to a portion of the medial side portion, at least a portion of the lateral side portion, or both of the respective medial and lateral side portions.

8. The ankle foot orthosis of claim 1, further comprising a plurality of mounting structures on the medial and the lateral side portions of the brace body.

9. The ankle foot orthosis of claim 1, wherein the sole portion is at least partially in a plane that is at least partially horizontal to the medial side portion and the lateral side portion.

10. The ankle foot orthosis of claim 1, wherein the sole portion is in a plane at least partially horizontal to the medial and lateral sides portions.

11. The ankle foot orthosis of claim 1, wherein the brace body further comprises a heel portion.

12. The ankle foot orthosis of claim 11, wherein the outer layer substantially covers the inner lining such that the outer layer covers the inner lining at the back portion, medial side portion, lateral side portion, sole portion and heel portion, and wherein the medial front edge and lateral front edge are composed of only the outer layer.

13. The ankle foot orthosis of claim 1, wherein the brace body is configured for use on a right foot or a left foot.

14. The ankle foot orthosis of claim 1, wherein the outer layer consists of a polyolefin elastomeric material selected from the group consisting of an ethylene/butene copolymer and an ethylene/octene copolymer.

15. The ankle foot orthosis of claim 14, wherein the outer layer substantially covers the inner lining such that the outer layer covers the inner lining at the back portion, medial side portion, lateral side portion and sole portion, and wherein the medial front edge and lateral front edge are composed of only the outer layer.

16. A method of manufacturing the ankle foot orthosis of claim 1, the method comprising:

forming the inner lining by forming the closed cell foam over a mold of a lower extremity including a foot;
forming the outer layer of the polyolefin elastomeric material over the foam inner lining;
setting a mounting structure for the closure mechanism into the outer layer, and
removing the mold to produce the ankle foot orthosis.

17. The method of claim 16, further comprising placing a lace loop on the mounting structure located over the foam material before forming the outer layer of the polyolefin elastomeric material.

18. The method of claim 17, further comprising adding a fastener to secure the mounting structure located over the foam material along with the polyolefin elastomeric material.

19. The method of claim 17, wherein the method further comprises cutting the outer layer of the polyolefin elastomeric material to expose the lace loop.

20. The method of claim 19, further comprising placing a lace through the lace loop.

21. The method of claim 16, further comprising providing one or more additional structures that are configured to enhance rigidity of at least one of a portion of the brace body and the closure mechanism.

22. An ankle foot orthosis comprising:
a brace body comprising closed cell foam inner lining bonded to an outer layer consisting essentially of a polyolefin elastomeric material selected from the group consisting of olefin ethylene/butene copolymer and an ethylene/octene copolymer, wherein the outer layer substantially covers the inner lining, the brace body further comprising:
a back portion;
a medial side portion having a medial front edge;
a lateral side portion having a lateral front edge;
a sole portion; and
a proximal edge;
the medial front edge and the lateral front edge being configured for an overlapping arrangement; and
a closure mechanism t tighten the ankle foot orthosis on a foot,
wherein the outer layer substantially covers the inner lining such that the outer layer covers the inner lining at the back portion, medial side portion, lateral side portion and sole portion, and wherein the medial front edge and lateral front edge are composed of only the outer layer.

23. The ankle foot orthosis of claim 22, further comprising a material layer bonded to the foam inner lining.

24. The ankle foot orthosis of claim 22, wherein the closure mechanism comprises laces, loops, hook and loop fastener, elastic, fasteners, or a combination thereof.

25. The ankle foot orthosis of claim 22, wherein at least a portion of the sole portion is at least partially perpendicular to a portion of the medial side portion, at least a portion of the lateral side portion, or both of the respective medial and lateral side portions.

26. The ankle foot orthosis of claim 22, further comprising a plurality of mounting structures on the medial and the lateral side portions of the brace body.

27. The ankle foot orthosis of claim 1, wherein the sole portion is at least partially in a plane that is at least partially horizontal to the medial side portion and the lateral side portion.

28. The ankle foot orthosis of claim 22, wherein the brace body further comprises a heel portion.

29. The ankle foot orthosis of claim 22, wherein the brace body is configured for use on a right foot or a left foot.

30. The angle foot orthosis of claim 22, wherein the ethylene/butene copolymer or ethylene/octene copolymer of the outer layer has a melt index at 190° C. of less than 0.5 to 30 g/10 min, a density of 0.857 to 0.910 g/cc, a melting range of 36° C. to 104° C., a Shore A Hardness of 56 to 96, and a flexural modulus from 3 to 110 MPa.

\* \* \* \* \*